US009101039B2

(12) United States Patent
Ikarashi et al.

(10) Patent No.: US 9,101,039 B2
(45) Date of Patent: Aug. 4, 2015

(54) RADIATION GENERATING APPARATUS AND RADIATION IMAGING SYSTEM

(71) Applicant: CANON KABUSHIKI KAISHA, Tokyo (JP)

(72) Inventors: Yoichi Ikarashi, Fujisawa (JP); Yoichi Ando, Inagi (JP); Yasuo Ohashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/059,279

(22) Filed: Oct. 21, 2013

(65) Prior Publication Data

US 2014/0112442 A1 Apr. 24, 2014

(30) Foreign Application Priority Data

Oct. 23, 2012 (JP) ................................ 2012-233426

(51) Int. Cl.
*A61B 6/08* (2006.01)
*H05G 1/02* (2006.01)
*H05G 1/58* (2006.01)

(52) U.S. Cl.
CPC ... *H05G 1/02* (2013.01); *H05G 1/58* (2013.01)

(58) Field of Classification Search
CPC ............ A61B 6/08; A61B 6/587; H01G 1/02; G21K 1/02; G21K 1/04
USPC ........................................................ 378/206
See application file for complete search history.

(56) References Cited

U.S. PATENT DOCUMENTS 5,388,138 A * 2/1995 Fujiwara ...................... 378/108
5,446,780 A * 8/1995 Aichinger et al. ........... 378/204

FOREIGN PATENT DOCUMENTS

JP 7-148159 A 6/1995

* cited by examiner

*Primary Examiner* — Courtney Thomas
(74) *Attorney, Agent, or Firm* — Canon USA Inc. IP Division

(57) ABSTRACT

A radiation generating apparatus includes a radiation generating unit and a diaphragm unit that functions as a projector-collimator configured to simulate a radiation field with a visible-light field. The diaphragm unit includes a light source configured to generate visible light, an optical lens configured to control a state of diffusion of the visible light emitted from the light source, and field-limiting blades. The light source and the optical lens are provided between a radiation emission window and the field-limiting blades. The light source is movable into and retractable from a path of radiation generated by the radiation generating unit.

18 Claims, 4 Drawing Sheets

RADIATION GENERATING APPARATUS AND RADIATION IMAGING SYSTEM

BACKGROUND OF THE INVENTION

1. Field of the Invention

The present invention generally relates to radiation apparatuses and systems thereof; more particularly it relates to a radiation generating apparatus including a movable diaphragm unit having a function of adjusting a radiation field passing therethrough, and to a radiation imaging system including such apparatus.

2. Description of the Related Art

In general, a radiation generating apparatus includes a movable diaphragm unit (hereinafter interchangeably referred to as "diaphragm unit" or "diaphragm"). The diaphragm unit has a function of adjusting the radiation field by blocking radiation that is unnecessary for imaging and thus reducing the exposure of a subject to radiation. The radiation field is adjusted by adjusting the size of an aperture defined by limiting blades that allows radiation to pass therethrough. Typically, the diaphragm unit has an additional function as a projector-collimator system in which the radiation field is simulated by a visible-light field so that the radiation field can be visually checked prior to imaging.

Japanese Patent Laid-Open No. 7-148159 discloses a movable X-ray diaphragm device which is used to adjust the size of an X-ray field and the size of a visible-light field to be made the same as each other. Specifically, the movable X-ray diaphragm device, by limiting with light blocking plates, makes the size of an X-ray field the same as the size of a visible light field emitted from a light source; the light source is larger than an X-ray focal point.

To adjust the size of the radiation field, the related-art diaphragm unit includes a reflector plate that is obliquely oriented. Therefore, the size of an envelope that houses the diaphragm unit becomes large, making it difficult to reduce the size of the radiation generating apparatus as a whole. The envelope is made of a material whose mass is large enough to block radiation. Therefore, as the envelope becomes larger, the mass of the envelope becomes larger too.

In such a related-art diaphragm unit employing a reflection radiation tube, a heel effect that may occur in the reflection radiation tube is advantageously reduced with the presence of the obliquely oriented reflector plate. In contrast, if a transmission radiation tube, which does not produce the heel effect, is employed, the variation in the quality of radiation worsens.

SUMMARY OF THE INVENTION

Embodiments of the present invention are directed to addressing the shortcomings of the related art to reduce the size and weight of a diaphragm unit and to improve the quality of radiation.

According to an aspect of the present invention, a radiation generating apparatus includes a radiation generating unit configured to generate radiation, and a diaphragm unit configured to limit a radiation field that is formed by the radiation emitted from the radiation generating unit. The diaphragm unit includes a light source configured to generate visible light with which the radiation field is simulated by a visible-light field, and an optical lens configured to control a state of diffusion of the visible light.

Further features of the present invention will become apparent from the following description of exemplary embodiments with reference to the attached drawings.

DESCRIPTION OF THE EMBODIMENTS

Embodiments of the radiation generating apparatus and a system thereof will now be described with reference to the attached drawings.

First Embodiment

Figure 1:
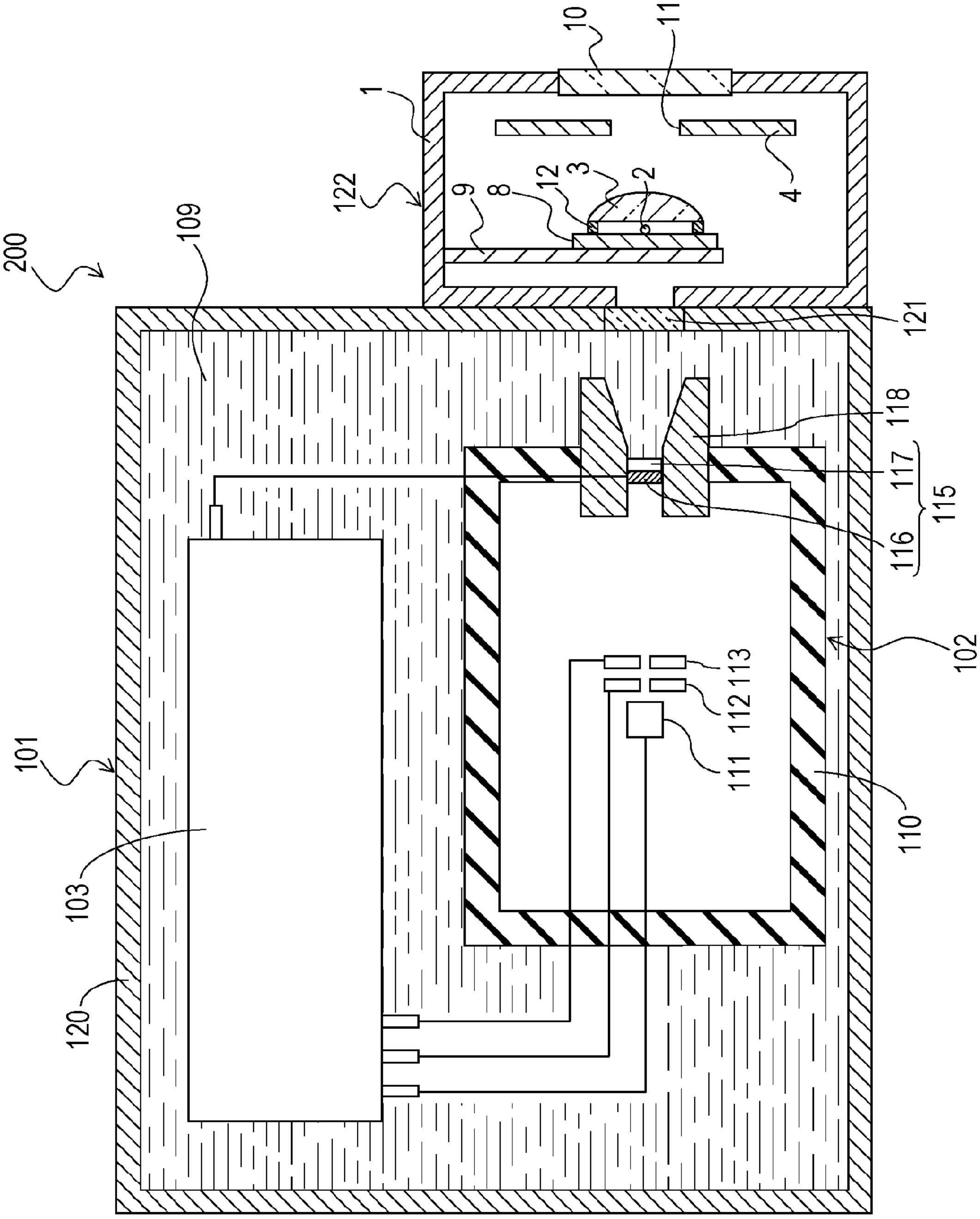
FIG. 1 is a schematic diagram of a radiation generating apparatus according to a first embodiment.
Figure 2B:
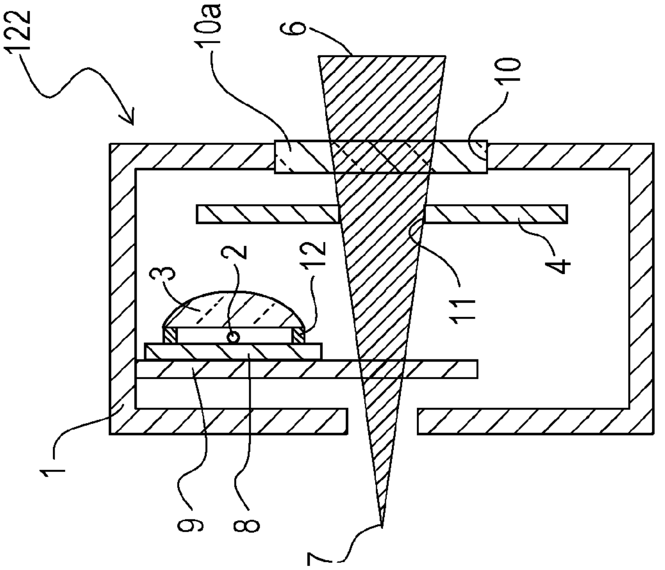
FIG. 2B is a schematic diagram of the diaphragm unit according to the first embodiment that is in a state where radiation is emitted.
Figure 2A:
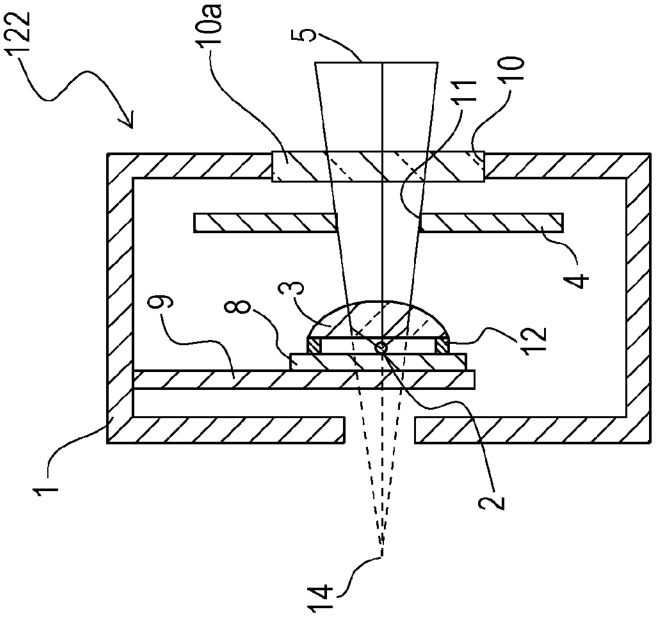
FIG. 2A is a schematic diagram of a diaphragm unit according to the first embodiment that is in a state where visible light is emitted.

Referring to FIGS. 1, 2A, and 2B, a radiation generating apparatus 200 includes a radiation generating unit 101 and a diaphragm unit 122.

The radiation generating unit 101 emits radiation from an emission window 121 provided at an opening of a container 120. The container 120 houses a radiation tube 102 as a radiation source, and a driving circuit 103 that controls the driving of the radiation tube 102. The space in the container 120 is filled with insulating liquid 109.

The container 120 may be made of a metallic material such as brass, iron, or stainless steel so as to provide sufficient strength as a container and a superior heat-releasing characteristic. The insulating liquid 109, which is electrically insulating liquid, has a function of maintaining the electrically insulating characteristic provided in the container 120 and a function as a medium that cools the radiation tube 102.

The radiation tube 102 is of a transmission type and causes electrons to collide against one side of a target 115 by accelerating electrons with a high voltage, thereby generating radiation emitted from the other side of the target 115 that is opposite the side against which electrons collide. The radiation tube 102 includes a radiation blocking member 118 that determines the direction of emission of the radiation toward the outside. The target 115 is provided in a cylindrical opening provided in the radiation blocking member 118. The radiation blocking member 118 blocks unnecessary radiation and may be made of lead or tungsten. While the first embodiment employs such a transmission radiation tube, the present disclosure is also applicable to a radiation generating apparatus employing a reflection radiation tube.

The target 115 includes a supporting substrate 117 made of diamond, and a target layer 116 provided on the supporting substrate 117 and configured to generate radiation when electrons are applied thereto. The target layer 116 is made of a material such as tungsten, tantalum, or molybdenum. The target layer 116 is electrically connected to the driving circuit 103 and forms a part of an anode.

A vacuum chamber 110 has a body in the form of an insulating tube made of an insulating material such as glass or ceramic so as to maintain a vacuum state thereinside and to electrically insulate a cathode 111 and the anode from each other. The pressure inside the vacuum chamber 110 is reduced so that the cathode 111 functions as an electron source. The degree of vacuum in the vacuum chamber 110 may be set to about $10^{-4}$ Pa to $10^{-8}$ Pa.

The cathode 111 faces toward the target layer 116. The cathode 111 may be a hot cathode such as a tungsten filament or an impregnated cathode, or a cold cathode such as a carbon nanotube. The cathode 111, a grid electrode 112, and a lens electrode 113 are each electrically connected to the driving circuit 103, and predetermined voltages are to be applied thereto. A voltage Va that is to be applied between the cathode 111 and the target layer 116 ranges from about 10 kV to 150 kV, varying with the use of the radiation.

When appropriate voltages are applied to the cathode 111, the grid electrode 112, the lens electrode 113, and the target layer 116, electrons are drawn from the cathode 111 by an electric field produced by the grid electrode 112. The electrons thus drawn are converged by the lens electrode 113 and are incident on the target layer 116 of the target 115, where radiation is generated. The radiation thus generated travels through the emission window 121 and is emitted into the diaphragm unit 122.

The diaphragm unit 122 includes an envelope 1, radiation limiting blades (hereinafter referred to as limiting blades or field-limiting blades) 4, a light source 2, an optical lens 3, and a movable mechanism 9.

The envelope 1 is provided over and encloses the emission window 121 of the container 120 and houses the above members thereinside. A side of the envelope 1 that is opposite a side thereof facing the emission window 121 has an opening 10 (envelope opening) that allows the radiation emitted from the radiation generating unit 101 to pass therethrough. A transparent plate 10*a* is provided in the envelope opening 10. The transparent plate 10*a* does not block the visible light or the radiation, but seals the envelope from environmental elements, such as dust and humidity.

The envelope 1 may be made of a radiation blocking material so that scattered radiation is blocked. Examples of radiation blocking material include metals such as lead, tungsten, and tantalum, and alloys of any of the foregoing metals. Alternatively, the envelope 1 may be made of a metal such as aluminum or a synthetic resin that does not satisfactorily block radiation, and, instead, a sheet that satisfactorily blocks radiation may be provided over the envelope 1. Thus, the envelope 1 can satisfactorily block radiation. Examples of such a sheet include a resin sheet containing tungsten powder.

Referring now to FIGS. 2A and 2B, the limiting blades 4 are made of a radiation blocking material and define an aperture 11 in the center thereof. The aperture 11 allows radiation and visible light to pass therethrough. The radiation that is emitted from the radiation generating unit 101 passes through the aperture 11 and is emitted to the outside through the envelope opening 10, thereby forming a radiation field 6. The size of the aperture 11 defined by the limiting blades 4 is adjustable. Accordingly, the size of the radiation field 6 is adjustable.

The limiting blades 4 may include, for example, two plates each having a cut or a hole. The two plates overlap each other while being slidable with respect to each other such that the cuts or the holes thereof overlap each other to form the aperture 11. In such a case, a portion where the cuts or the holes overlap each other is provided as the aperture 11. The size and shape (cross-section) of the aperture 11 is adjustable by sliding the two plates with respect to each other. Alternatively, the limiting blades 4 may include three or more plates that are provided in a circular arrangement in such a manner as to form the aperture 11 by slidably overlapping with one another. As another alternative, the limiting blades 4 may form a structure that is similar to a shutter of a camera. The cross-sectional shape of the aperture 21 may be substantially circular or polygonal.

The light source 2 and the optical lens 3 in combination form a projector-collimator that simulates the radiation field 6 as a visible-light field 5. The light source 2 and the optical lens 3 are provided on a path of the radiation and between the emission window 121 and the limiting blades 4.

The light source 2 emits visible light and may be any of incandescent lamp, a halogen lamp, a xenon lamp, a light-emitting diode (LED), and the like. In particular, an LED is suitable as the light source 2 because it tends to be small. The light source 2 is provided between the optical lens 3 and a supporting plate 8 that is provided on the rear side (a side facing toward the emission window 121) of the optical lens 3.

The optical lens 3 is provided for controlling the visible light that has been incident thereon from the light source 2 to be diffused in such a state that the visible-light field 5 is formed in an appropriate form. The optical lens 3 is a convex lens that converges visible light. The optical lens 3 is joined to the supporting plate 8 with a frame-shaped joining member 12 interposed therebetween. The light source 2 is provided in a space between the supporting plate 8 and the optical lens 3 and enclosed by the joining member 12. The optical path length of the visible light emitted through the optical lens 3 is shorter than the optical path length of the radiation (the radiation length).

The optical lens 3 and the target 115 are positioned such that a focal point 14 of the optical lens 3 coincides with a focal point 7 of the radiation. The optical lens 3 may be positioned such that the axis of the radiation that is to be applied to the radiation field 6 coincides with the optical axis of the optical lens 3. Such an arrangement facilitates an accurate simulation of the radiation field 6 as the visible-light field 5. If such an arrangement cannot be realized, visible-light limiting blades configured to limit the area of application of the visible light that forms the visible-light field 5 may be provided on the inside or the outside of the envelope 1, whereby the size and shape of the visible-light field 5 may be controlled. The axis of radiation referred to herein corresponds to a straight line connecting the focal point 7 of the radiation and the center of the radiation field 6 that is formed when the limiting blades 4 are opened to their maximum. The focal point 7 of the radiation corresponds to the center of a radiation generating area, or the center of an electron-beam application area in the target layer 116. Supposing that the radiation field 6 is a plate having a uniform thickness, the center of the radiation field 6 corresponds to the center of gravity of the plate (if the radiation field 6 has a square shape, the center of the square shape). Supposing that the electron-beam application area is a plate having a uniform thickness, the center of the electron-beam application area corresponds to the center of gravity of the plate (if the electron-beam application area has a circular shape, the center of the circular shape).

The optical lens 3 may be made of a material, such as glass, polymethyl methacrylate (PMMA), or acrylic resin, having a high transmittance with respect to visible light and radiation. The optical lens 3 may have either a biconvex shape or a plano-convex shape. The surface of the optical lens 3 may be either spherical or aspherical. To make the radiation field 6 and the visible-light field 5 coincide with each other with high accuracy, the optical lens 3 may be an aspherical lens that is formed with consideration for aberrations.

To reduce the size of the diaphragm unit 122, the focal length of the optical lens 3 may be set as short as possible, specifically, 5 mm to 30 mm. To collect visible light emitted from the light source 2 as much as possible, the diameter of the optical lens 3 may be set to 5 mm to 30 mm. To reduce the size of the diaphragm unit 122, the thickness of the optical lens 3 at the center may be set as thin as possible, specifically, 1 mm to 20 mm.

The supporting plate 8 is retractable from the path of the radiation by a movable mechanism 9. The movable mechanism 9 may include a rail provided at a position deviating from the path of the radiation that forms the radiation field 6. In this case, the supporting plate 8 is held on the rail in such a manner as to be slidable along the rail. With the sliding of the supporting plate 8, the light source 2 and the optical lens 3 are both movable into and retractable from the path of the radiation.

In using the radiation generating apparatus 200, prior to the emission of radiation, the radiation field 6 is simulated by the visible-light field 5, whereby the radiation field 6 is checked visually. The visible light emitted from the light source 2 is collected by the optical lens 3, passes through the aperture 11 defined by the limiting blades 4, and forms the visible-light field 5. In this state, the size of the aperture 11 defined by the limiting blades 4 is adjusted so that the size of the visible-light field 5 becomes the same as the size of a desired radiation field 6. After the size of the radiation field 6 is determined, the light source 2 is turned off and the supporting plate 8 is retracted. Then, the radiation generating unit 101 is activated.

The radiation that has been emitted from the radiation generating unit 101 toward the diaphragm unit 122 passes through the aperture 11 defined by the limiting blades 4 and is applied to the radiation field 6 that has been determined as described above.

The diaphragm unit 122 does not include an obliquely oriented reflector mirror that is employed in the related art. Therefore, the diaphragm unit 122 does not need to reduce the heel effect that can be reduced in the case where a reflection radiation tube is employed. In this manner, the diaphragm unit 122 suppresses variation in the quality of radiation that may occur in a case where a transmission radiation tube is employed. Hence, the first embodiment employs the radiation generating unit 101 including the radiation tube 102 that is of a transmission type.

Second Embodiment

A diaphragm unit 122 according to a second embodiment will now be described with reference to FIGS. 3A and 3B.

The diaphragm unit 122 according to the second embodiment includes a fixed member 13. The optical lens 3 is secured to the fixed member 13.

The light source 2 is secured to the supporting plate 8. The supporting plate 8 is movable into and retractable from the path of the radiation by the movable mechanism 9, as in the case of the diaphragm unit 122 illustrated in FIGS. 2A and 2B. However, since the optical lens 13 is secured to the fixed member 13, it remains fixed in the path of radiation.

The shape and size of the fixed member 13 are determined in accordance with the shape and size of the optical lens 3. To suppress the increase in the weight of the diaphragm unit 122 as much as possible, the fixed member 13 may be made of a light-mass material. The optical lens 3 is secured to the fixed member 13 with any of adhesive, nails, screws, and the like. The fixed member 13 may alternatively be made of transparent glass or synthetic resin. In that case, the optical lens 3 may be integrated with the fixed member 13 as a part of the fixed member 13.

The light source 2 needs to be provided with a metal wire or the like through which power is supplied thereto. However, such a metallic material is one of factors that hinder the application of radiation. To avoid this, the optical lens 3 is made of a material having a relatively high transmittance with respect to radiation. In the second embodiment, only the light source 2 is retractable by the movable mechanism 9, with the optical lens 3 being fixed on the path of the radiation that forms the radiation field 6, whereby the number of movable members is minimized. Note that, however, the uniformity in the radiation applied to the radiation field 6 is higher in the case where both the light source 2 and the optical lens 3 are retractable.

Third Embodiment

Figure 4:
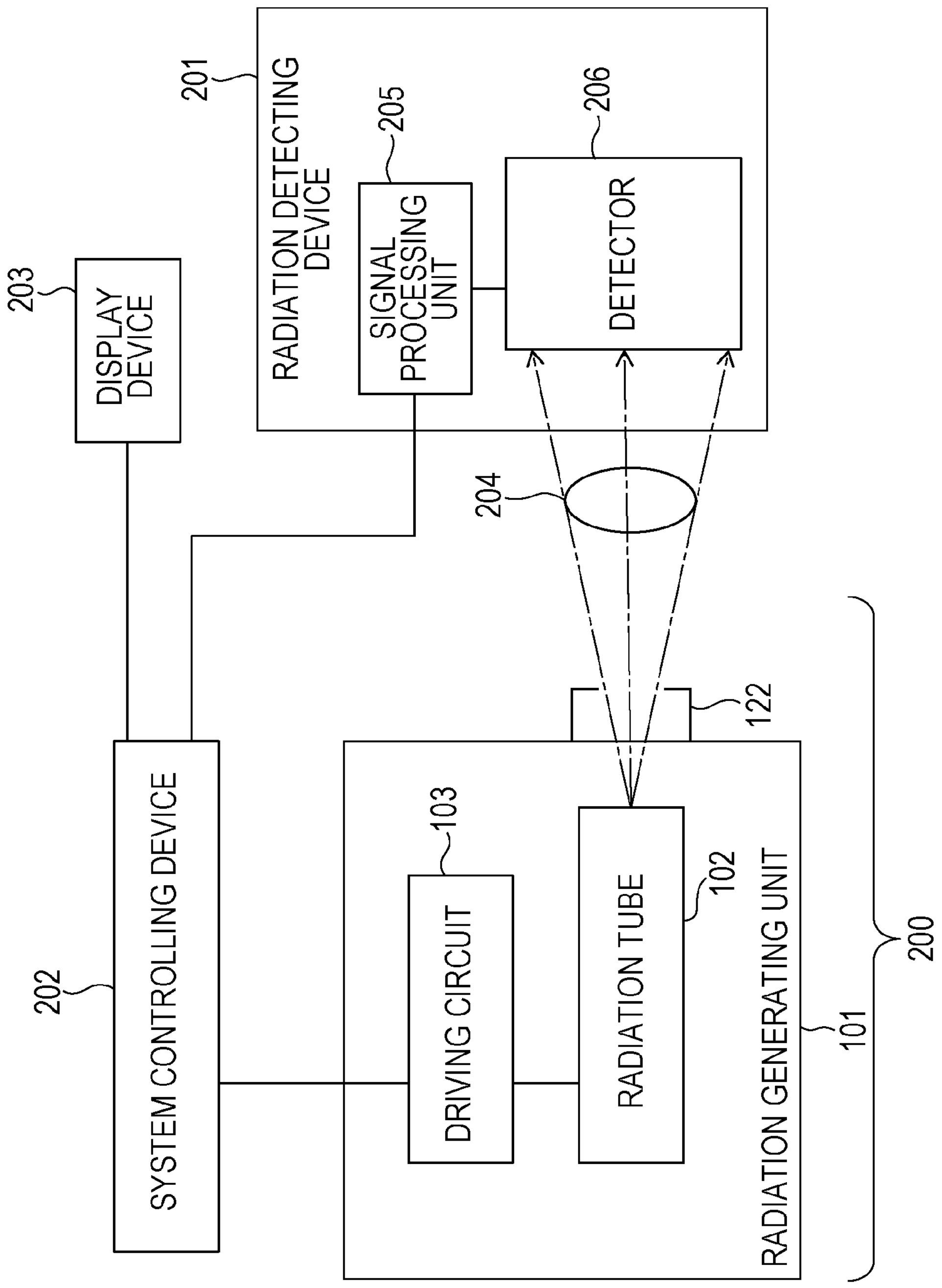
FIG. 4 is a block diagram of a radiation imaging system including a radiation generating apparatus according to a third embodiment.

A radiation imaging system according to a third embodiment will now be described with reference to FIG. 4.

A system controlling device 202 controls the radiation generating apparatus 200 in conjunction with a radiation detecting device 201. The driving circuit 103, which is controlled by the system controlling device 202, outputs control signals to the radiation tube 102. In accordance with the control signals, the state of radiation that is emitted from the radiation generating apparatus 200 is controlled. The radiation that has been emitted from the radiation generating apparatus 200 is transmitted through an examination object 204 and is detected by a detector 206. The detector 206 converts the detected radiation into an image signal and outputs the image signal to a signal processing unit 205. The signal processing unit 205, which is controlled by the system controlling device 202, processes the image signal in a predetermined procedure and outputs the processed image signal to the system controlling device 202. The system controlling device 202 generates a display signal, which is for displaying an image on a display device 203, on the basis of the processed image signal and outputs the display signal to the display device 203. The display device 203 displays the image that is based on the display signal as an image of the examination object 204 on its screen. Typical examples of the radiation include X-rays. Accordingly, the radiation generating apparatus 200 and the radiation imaging system according to the above embodiments can be used as an X-ray generating apparatus and an X-ray imaging system. An X-ray imaging system can be used in nondestructive inspection of industrial products or pathological diagnosis of human bodies or animals.

EXAMPLES

Working Example 1

The diaphragm unit 122 illustrated in FIGS. 2A and 2B were manufactured.

The envelope 1 was of size 100 mm×50 mm×70 mm. A resin sheet containing tungsten powder was pasted onto the inner surface of the envelope 1 so as to prevent leakage of scattered radiation.

The light source 2 was a chip LED of side 2 mm and was soldered onto the supporting plate 8, which had been wired in advance.

With consideration for the influence of aberrations, a plano-convex, aspherical glass lens having a focal length of 18 mm, a diameter of 24 mm, and a thickness of 10 mm was used as the optical lens 3. The optical lens 3 was provided integrally with the light source 2 with the supporting plate 8 interposed therebetween. In visually checking the radiation field 6, the light source 2 and the optical lens 3 were positioned such that the focal point 14 of visible light having been transmitted through the optical lens 3 substantially coincided with the focal point 7 of the radiation, whereby the optical path length of the visible light were made shorter than the optical path length of the radiation. Furthermore, the axes of the radiation and the visible light were made to coincide with each other.

The supporting plate 8 were included in the movable mechanism 9 in such a manner as to be slidable along a slide groove (not illustrated). In visually checking the radiation field 6 by using the visible light, the light source 2 and the optical lens 3 were moved by the movable mechanism 9 to such positions that the focal point 7 of the radiation and the focal point 14 of the visible light coincided with each other. In emitting the radiation, the light source 2 and the optical lens 3 were retracted to the outside of the area where the radiation forming the radiation field 6 travelled.

The diaphragm unit 122 configured as described above was attached to the radiation generating unit 101 that is of a transmission type, whereby a radiation imaging system was obtained. When the operation of the radiation imaging system was tested, it was confirmed that a visible-light field 5 substantially coinciding with the radiation field 6 was formed.

When a radiation imaging operation was performed, a good image with no heel effect was obtained. The total weight of the diaphragm unit 122 was about 500 g, which was far lighter than the related-art product.

Comparative Example 1

A visible light source included in a related-art diaphragm unit was positioned such that the optical path length of the radiation and the optical path length of the visible light became the same so that the visible-light field substantially coincided with the radiation field. The visible light was applied to the radiation field after being reflected by an obliquely oriented reflector mirror. With the presence of the obliquely oriented reflector mirror, the size of the envelope of the diaphragm unit was large. Specifically, the envelope was of size 200 mm×200 mm×150 mm with a weight of about 2 kg.

A transmission radiation generating unit was combined with the above diaphragm unit including the reflector mirror, whereby a radiation generating apparatus was obtained. Using the radiation generating apparatus, a radiation imaging system was obtained. When an image was taken with the radiation imaging system, the image had gradation under the influence of the heel effect caused by the obliquely oriented reflector mirror.

Working Example 2

Figure 3A:
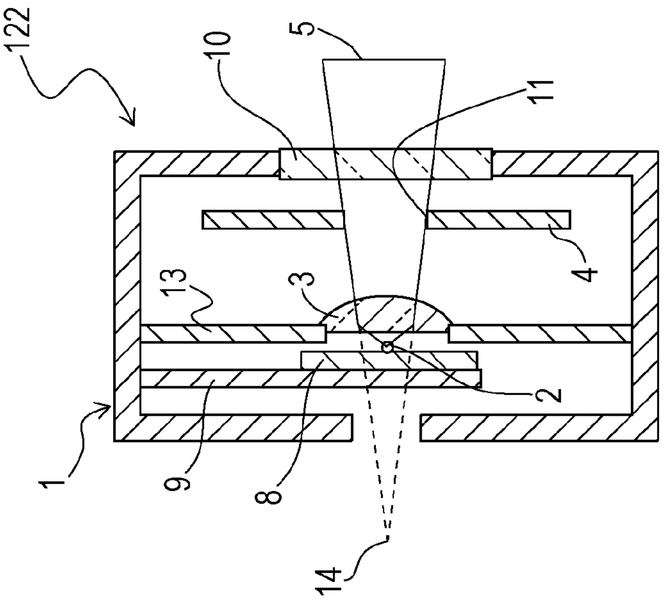
FIG. 3A is a schematic diagram of a diaphragm unit, according to a second embodiment, in a state where visible light is emitted.
Figure 3B:
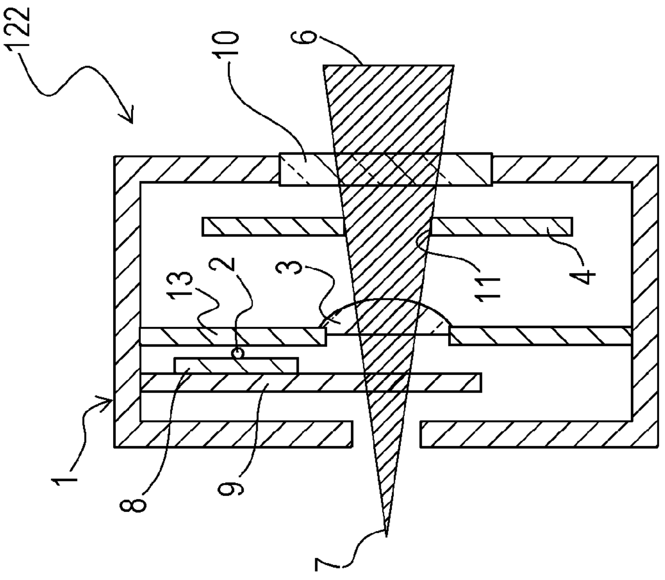
FIG. 3B is a schematic diagram of the diaphragm unit, according to the second embodiment, in a state where radiation is emitted.

The diaphragm unit 122 illustrated in FIGS. 3A and 3B was manufactured.

The envelope 1 was of size 100 mm×50 mm×80 mm. A resin sheet containing tungsten powder was pasted onto the inner surface of the envelope 1 so as to prevent leakage of scattered radiation.

The light source 2 was a chip LED of side 2 mm and was soldered onto the supporting plate 8, which had been wired in advance.

With consideration for the influence of aberrations, a plano-convex, aspherical glass lens having a focal length of 18 mm, a diameter of 24 mm, and a thickness of 10 mm was used as the optical lens 3. The optical lens 3 was attached to the envelope 1 with the fixed member 13 interposed therebetween such that the axes of the radiation and the visible light transmitted through the optical lens 3 coincided with each other. In visually checking the radiation field 6, the light source 2 and the optical lens 3 were positioned such that the effective focal point 14 of the visible light having been transmitted through the optical lens 3 substantially coincided with the focal point 7 of the radiation, whereby the optical path length of the visible light were made shorter than the optical path length of the radiation.

The supporting plate 8 were included in the movable mechanism 9 in such a manner as to be slidable along a slide groove (not illustrated). The light source 2 was provided on the supporting plate 8. In visually checking the radiation field 6 by using the visible-light field 5, the light source 2 was moved by the movable mechanism 9 to such a position that the axes of the radiation and the visible light coincided with each other. In emitting the radiation, the light source 2 was retracted to the outside of the area where the radiation forming the radiation field 6 travelled.

The diaphragm unit 122 configured as described above was attached to a transmission radiation generating unit, whereby a radiation imaging system was obtained. When the operation of the radiation imaging system was tested, it was confirmed that a visible-light field 5 substantially coinciding with the radiation field 6 was formed.

When a radiation imaging operation was performed, a good image with no heel effect was obtained. The total weight of the diaphragm unit 122 was about 550 g, which was far lighter than the related-art product.

According to each of the embodiments described herein, the visible-light field is formed by the light source and the optical lens that are provided between the emission window and the limiting blades. Advantageously, the light source and the optical lens (or the light source alone) are movable into and retractable from the radiation path. Therefore, an obliquely oriented reflector mirror employed in the related art is omitted, whereby the size and weight of the radiation generating apparatus as a whole are reduced. Accordingly, the size and weight of the radiation imaging system as a whole are reduced. Furthermore, since a transmission radiation tube that does not produce the heel effect is employed, nonuniformity in the quality of radiation is reduced.

While aspects of the present invention have been described with reference to exemplary embodiments, it is to be understood that the disclosed exemplary embodiments are not limiting. The scope of the following claims is to be accorded the broadest reasonable interpretation so as to encompass all modifications and equivalent structures and functions.

This application claims the benefit of Japanese Patent Application No. 2012-233426, filed Oct. 23, 2012, which is hereby incorporated by reference herein in its entirety.

What is claimed is:

1. A radiation generating apparatus comprising:

a radiation generating unit configured to generate radiation; and a diaphragm unit configured to limit a radiation field that is formed by the radiation emitted from the radiation generating unit, wherein the diaphragm unit includes a light source configured to generate visible light with which the radiation field is simulated by a visible-light field;

an optical lens configured to control a state of diffusion of the visible light, and a pair of field-limiting blades configured to limit the radiation field, wherein the radiation generating unit includes a radiation tube provided thereinside and configured to generate radiation;

an emission window through which the radiation generated by the radiation tube is emitted, and an envelope provided over and enclosing the emission window; and wherein the light source and the optical lens are provided between the emission window and the pair of field-limiting blades, and the light source is movable into and retractable from a path of the radiation by a movable mechanism.

2. The radiation generating apparatus according to claim 1, wherein an imaginary focal point of the optical lens corresponding with a visible light emitting point and a focal point of the radiation coincide with each other.

3. The radiation generating apparatus according to claim 1, wherein the optical lens is provided such that an axis of the radiation that is applied to the radiation field coincides with an optical axis of the optical lens.

4. The radiation generating apparatus according to claim 1, wherein the optical lens is movable into and retractable from the path of the radiation.

5. The radiation generating apparatus according to claim 1, wherein the optical lens is fixed in the path of the radiation.

6. The radiation generating apparatus according to claim 1, wherein the optical lens is a convex lens.

7. The radiation generating apparatus according to claim 1, wherein the optical lens is an aspherical lens.

8. The radiation generating apparatus according to claim 1, wherein the light source is a light-emitting diode.

9. A radiation imaging system comprising:

a radiation generating apparatus according to claim 1;

a radiation detecting device configured to detect the radiation having been emitted from the radiation generating apparatus and having been transmitted through an examination object; and a control device configured to control the radiation generating apparatus in conjunction with the radiation detecting device.

10. The radiation generating apparatus according to claim 1, wherein the pair of field-limiting blades is configured to be adjustable in a distance therebetween.

11. An X-ray generating apparatus comprising:

an X-ray generating unit having an emission window through which an X-ray is emitted; and a diaphragm unit configured to limit an irradiation field that is formed by the radiation emitted from the X-ray generating unit, wherein the diaphragm unit includes a light source configured to generate visible light with which the irradiation field is simulated by a visible-light field;

an optical lens configured to control a state of diffusion of the visible light; and a pair of field-limiting blades configured to limit the irradiation field, and wherein the light source and the optical lens are located in that order along an irradiation path from the emission window toward the pair of field-limiting blades.

12. The X-ray generating apparatus according to claim 11, wherein the light source is configured to be movable into and retractable from the irradiation path.

13. The X-ray generating apparatus according to claim 11, wherein the pair of field-limiting blades is configured to be adjustable in a distance therebetween.

14. The X-ray generating apparatus according to claim 11, wherein the X-ray generating unit includes:

an X-ray tube configured to generate X-ray; and an envelope housing the X-ray tube and having the emission window in front of the X-ray tube.

15. The X-ray generating apparatus according to claim 14, wherein an imaginary focal point of the optical lens corresponding with a visible light emitting point and a focal point of the X-ray tube coincide with each other.

16. The X-ray generating apparatus according to claim 11, wherein the optical lens is an aspherical lens.

17. The X-ray generating apparatus according to claim 11, wherein the X-ray tube is a transmission type X-ray tube.

18. A radiography system comprising:

an X-ray generating apparatus according to claim 11 an X-ray detecting device configured to detect the X-ray having been emitted from the X-ray generating apparatus and having been transmitted through an examination object; and a control device configured to control the X-ray generating apparatus in conjunction with the X-ray detecting device.

* * * * *